United States Patent
Viertelhaus et al.

(10) Patent No.: US 10,105,355 B2
(45) Date of Patent: Oct. 23, 2018

(54) MULTI-COMPONENT CRYSTALS OF VISMODEGIB AND SELECTED CO-CRYSTAL FORMERS OR SOLVENTS

(71) Applicant: BASF SE, Ludwigshafen (DE)

(72) Inventors: Martin Viertelhaus, Mannheim (DE); Tiziana Chiodo, Mannheim (DE); Beate Salvador, Ellerstadt (DE); Marcus Vossen, Limburgerhof (DE); Andreas Hafner, Gelterkinden (CH); Tobias Hintermann, Therwil (CH); Walter Weishaar, Gruenstadt (DE); Rolf Hellmann, Lustadt (DE)

(73) Assignee: BASF SE (DE)

( * ) Notice: Subject to any disclaimer, the term of this patent is extended or adjusted under 35 U.S.C. 154(b) by 0 days.

(21) Appl. No.: 15/501,908

(22) PCT Filed: Aug. 3, 2015

(86) PCT No.: PCT/EP2015/067822
§ 371 (c)(1),
(2) Date: Feb. 6, 2017

(87) PCT Pub. No.: WO2016/020324
PCT Pub. Date: Feb. 11, 2016

(65) Prior Publication Data
US 2017/0216266 A1 Aug. 3, 2017

(30) Foreign Application Priority Data

Aug. 7, 2014 (EP) ..................... 14180255

(51) Int. Cl.
*C07D 213/40* (2006.01)
*A61K 31/4402* (2006.01)

(52) U.S. Cl.
CPC ........ *A61K 31/4402* (2013.01); *C07D 213/40* (2013.01)

(58) Field of Classification Search
None
See application file for complete search history.

(56) References Cited

U.S. PATENT DOCUMENTS 7,888,364 B2  2/2011 Gunzner et al.

FOREIGN PATENT DOCUMENTS

WO  WO-06028959 A2  3/2006
WO  WO-2006028958 A2  3/2006

OTHER PUBLICATIONS

Authors et. al.: Disclosed Anonymously, IP.com No. IPCOM000228845D, A Crystalline Form of (2-chloro-N-[4-chloro-3-(2-pyridinyl)phenyl]-4 (methylsulfonyl)-benzamide), An IP.com Prior Art Database Technical Disclosure, IP.com Electronic Publication, pp. 1 and 2, Date: Jul. 10 (Year: 2013).*
Aitipamula, S., et al, "Polymorphs, Salts, and Cocrystals: What's in a Name?", Crystal Growth & Design, vol. 12, No. 5, (2012), pp. 2147-2152.
International Search Report for PCT/EP2015/067822 dated Sep. 30, 2015.
Written Opinion of the International Searching Authority for PCT/EP2015/067822 dated Sep. 30, 2015.

* cited by examiner

*Primary Examiner* — Zinna Northington Davis
(74) *Attorney, Agent, or Firm* — Drinker Biddle & Reath LLP

(57) ABSTRACT

The present invention primarily relates to multi-component crystals comprising a compound of formula 1

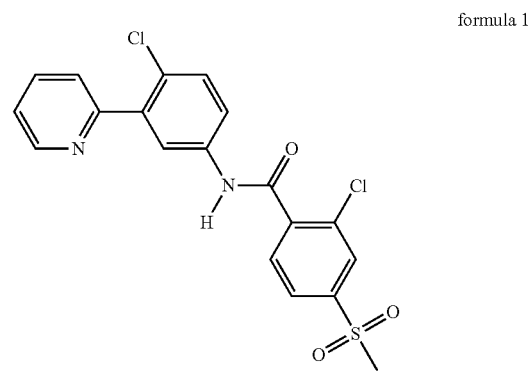

formula 1 and a second compound selected from the group consisting of co-crystal formers and solvents. The invention is further related to pharmaceutical compositions comprising such multi-component crystals. Furthermore, the invention relates to processes for preparing said multi-component crystals. The invention also relates to several aspects of using said multi-component crystals or pharmaceutical compositions to treat a disease.

16 Claims, 7 Drawing Sheets

MULTI-COMPONENT CRYSTALS OF VISMODEGIB AND SELECTED CO-CRYSTAL FORMERS OR SOLVENTS

CROSS-REFERENCE TO RELATED APPLICATIONS

This application is a national stage application (under 35 U.S.C. § 371) of PCT/EP2015/067822, filed Aug. 3, 2015, which claims benefit of European Application No. 14180255.3, filed Aug. 7, 2014, both of which are incorporated herein by reference in their entirety.

Vismodegib was first disclosed in WO Patent Publication No. 06/028959. Vismodegib, chemically 2-Chloro-N-(4-chloro-3-pyridin-2-ylphenyl)-4-methylsulfonylbenzamide, is represented by the following structure:

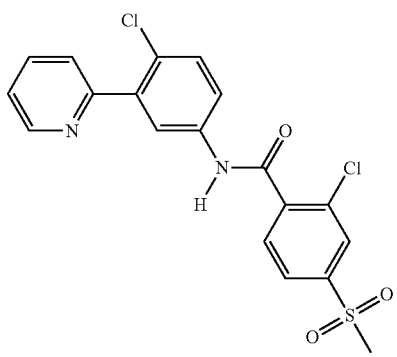

formula 1

Vismodegib is an active pharmaceutical ingredient produced by Genentech (Roche) and sold under the trade name Erivedge® (which contains crystalline Vismodegib as the active ingredient). Erivedge® is an oral Hedgehog signaling pathway inhibitor approved for the treatment of basal-cell carcinoma (BCC).

The present invention primarily relates to multi-component crystals comprising a compound of formula 1 (cf. above) and a second compound selected from the group consisting of co-crystal formers and solvents.

The invention is further related to pharmaceutical compositions comprising said multi-component crystals. Furthermore, the invention also relates to processes for preparing said multi-component crystals. The invention also relates to several aspects of using said multi-component crystals or pharmaceutical compositions to treat a disease. Further details as well as further aspects of the present invention will be described herein below.

Vismodegib is a BCS class II compound with a high permeability but a low solubility where enhanced solubility or dissolution rates can lead to a significant advantage in respect to bio-availability.

Vismodegib is known to exist as crystalline free base. Salts of Vismodegib are mentioned in U.S. Pat. No. 7,888,364 B2 but not specified. In particular, the HCl salt is mentioned as intermediate but not characterized. Co-crystals or solvates are not reported at all.

The solubility of Vismodegib is reported to be 0.1 µg/mL at pH 7 and 0.99 mg/mL at pH 1 for Erivedge®. The absolute bio-availability after single dose is reported to be 31.8% and the exposure is not linear at single doses higher than 270 mg. Erivedge® capsules do not have a food label. The estimated elimination half-life (t½) after continuous once-daily dosing is 4 days and 12 days after a single dose treatment (Highlights of Prescribing Information: ERIVEDGE® (vismodegib) capsule for oral use; Revised: January 2012).

The discovery and preparation of new co-crystals or solvates offer an opportunity to improve the performance profile of a pharmaceutical product. It widens the reservoir of techniques/materials that a formulation scientist can use for designing a new dosage form of an active pharmaceutical ingredient (API) with improved characteristics. One of the most important characteristics of an API such as Vismodegib is the bio-availability which is often determined by the aqueous solubility.

A compound like Vismodegib may give rise to a variety of crystalline forms having distinct crystal structures and physical characteristics like melting point, X-ray diffraction pattern, infrared spectrum, Raman spectrum and solid state NMR spectrum. One crystalline form may give rise to thermal behavior different from that of another crystalline form. Thermal behavior can be measured in the laboratory by such techniques as capillary melting point, thermogravimetry (TG), and differential scanning calorimetry (DSC) as well as content of solvent in the crystalline form, which have been used to distinguish polymorphic forms.

Multi-component crystals comprising Vismodegib and selected co-crystal formers or solvents may improve the dissolution kinetic profile and allow to control the hygroscopicity of Vismodegib.

Therefore, there is a need for multi-component crystals comprising Vismodegib that avoid the above disadvantages. In particular, it is an object of the present invention to provide multi-component crystals of Vismodegib with optimized manufacture, formulation, stability and/or biological efficacy.

SUMMARY OF THE INVENTION

The invention provides novel multi-component crystals comprising a compound of formula 1 (INN: Vismodegib)

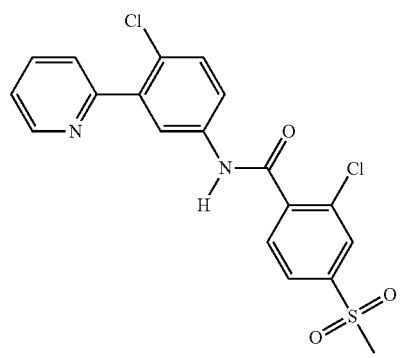

formula 1 and
a second compound selected from the group consisting of co-crystal formers and solvents.

Novel pharmaceutical compositions containing these multi-component crystals and processes for manufacture of such multi-component crystals as well as aspects of using said multi-component crystals or compositions to treat a disease are also described herein.

DETAILED DESCRIPTION OF THE INVENTION

Figure 1:
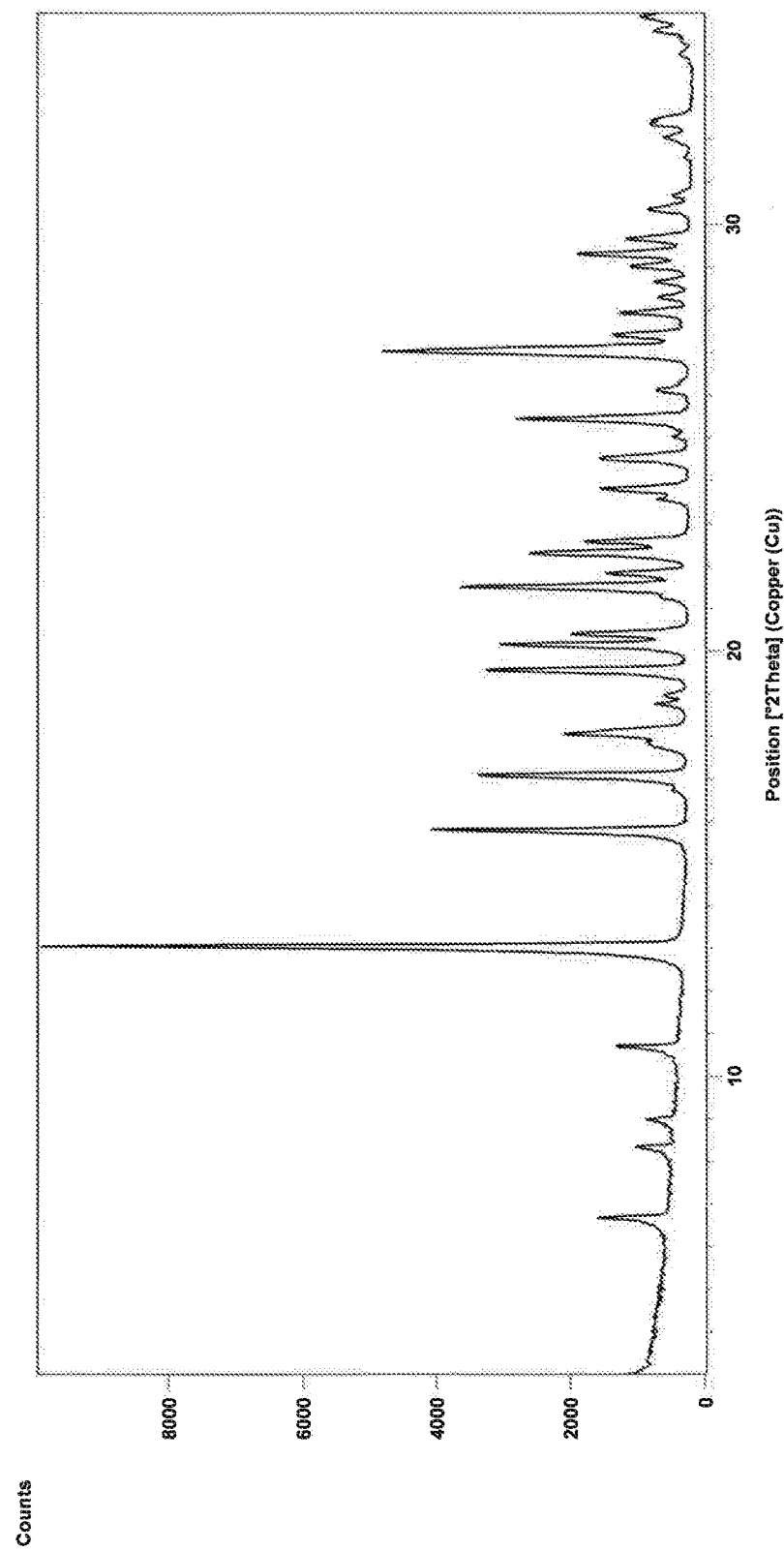
FIG. 1: PXRD pattern of Vismodegib maleic acid co-crystal 1:2; Cu Kα radiation.

The present invention is directed to multi-component crystals comprising a compound of formula 1 (INN: Vismodegib)

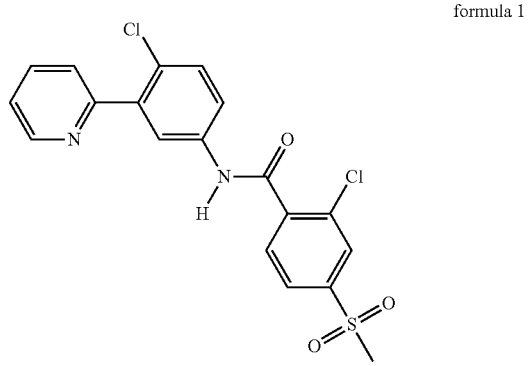 [SMILES: CS(=O)(=O)c1ccc(C(=O)Nc2ccc(Cl)c(-c3ccccn3)c2)c(Cl)c1]

formula 1 and
a second compound selected from the group consisting of co-crystal formers and solvents.

The herein disclosed solid forms (multi-component crystals comprising Vismodegib and selected co-crystal formers or solvents) give rise to advantages in comparison to Vismodegib with respect to solubility, dissolution rate, hygroscopicity, storage stability, bioavailability, purity, purification etc. This means the new solid forms have higher solubility, higher dissolution rate, lower hygroscopicity, better storage stability, higher bioavailability, bioavailability with less variability, higher purity or better purification properties.

In the meaning of the present invention a co-crystal former is any compound in the solid state that forms a co-crystal with the compound of formula 1. Accordingly, in the meaning of the present invention a solvent is any compound in the liquid state.

Preferably, the co-crystal former is selected from the group consisting of maleic acid, N-cyclohexyl-sulfamic acid, sorbitol and xylitol. Preferably, the solvent is selected from the group consisting of benzylamine and triethanolamine.

Preferably, the multi-component crystals are characterized in that the molar ratio of Vismodegib to the second compound is in the range of from 3:1 to 1:3.

In a preferred embodiment, the second compound is maleic acid and a single multi-component crystal has a PXRD pattern with at least one, preferably more or all characteristic peak(s) (expressed in °2θ±0.2 °2θ (CuKα radiation)) selected from the following peaks located at 6.7, 10.7, 13.1, 15.8, 18.0, 19.5, 20.1, 20.4, 21.8, 22.3, 25.4, 26.1, 27.0, 27.4, 27.9, 28.3, 29.0, 29.3.

In another preferred embodiment, the second compound is N-cyclohexyl-sulfamic acid and a single multi-component crystal has a PXRD pattern with at least one, preferably more or all characteristic peak(s) (expressed in °2θ±0.2 °2θ (CuKα radiation)) selected from the following peaks located at 7.9, 11.3, 12.1, 13.4, 15.8, 16.0, 16.8, 17.6, 18.6, 19.0, 19.9, 21.3, 21.7, 22.0, 24.6, 24.8, 26.1, 26.7 or selected from the following peaks located at 6.4, 12.8, 18.5, 19.2, 21.6, 26.0.

In another preferred embodiment, the second compound is sorbitol and a single multi-component crystal has a PXRD pattern with at least one, preferably more or all characteristic peak(s) (expressed in °2θ±0.2 °2θ (CuKα radiation)) selected from the following peaks located at 9.8, 11.4, 12.1, 13.4, 16.0, 16.9, 17.4, 17.7, 18.1, 19.1, 19.5, 20.0, 21.5, 22.0, 24.7, 24.9, 26.1, 26.7.

In another further preferred embodiment, the second compound is xylitol and a single multi-component crystal has a PXRD pattern with at least one, preferably more or all characteristic peak(s) (expressed in °2θ±0.2 °2θ (CuKα radiation)) selected from the following peaks located at 9.7, 11.4, 12.1, 13.4, 16.0, 16.8, 17.4, 17.6, 18.0, 19.0, 19.8, 21.5, 22.0, 22.5, 23.7, 24.6, 24.8, 26.1, 26.7, 27.0, 31.5, 32.9.

In another preferred embodiment, the second compound is benzylamine and a single multi-component crystal has a PXRD pattern with at least one, preferably more or all characteristic peak(s) (expressed in °2θ±0.2 °2θ (CuKα radiation)) selected from the following peaks located at 9.8, 11.3, 12.0, 13.5, 16.0, 16.7, 17.3, 17.6, 17.9, 18.9, 20.7, 21.5, 21.9, 22.7, 24.3, 24.7, 26.1, 26.8, 27.1, 28.3, 28.6.

In yet another preferred embodiment, the second compound is triethanolamine and a single multi-component crystal has a PXRD pattern with at least one, preferably more or all characteristic peak(s) (expressed in °2θ±0.2 °2θ (CuKα radiation)) selected from the following peaks located at 9.4, 10.7, 11.5, 12.1, 13.7, 14.3, 15.7, 16.0, 16.6, 17.3, 18.0, 18.9, 21.4, 22.2, 23.1, 23.9, 24.4, 25.6, 25.9, 27.3, 27.7, 28.4.

In a preferred embodiment of the present invention, the single multi-component crystal is selected from those characterized above, with a PXRD pattern showing all characteristic peaks listed above for the specific crystal.

Another object of the invention is a process for obtaining multi-component crystals according to the invention (as described herein) comprising the steps of:
a) providing a compound of formula 1 (INN: Vismodegib)

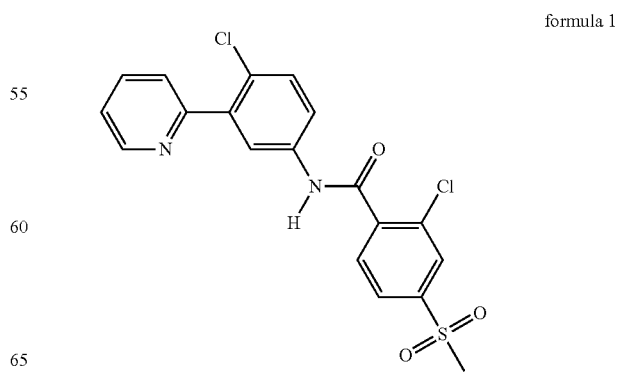

formula 1 as a solid or in solution;
b) adding maleic acid, N-cyclohexyl-sulfamic acid, sorbitol, xylitol, benzylamine or triethanolamine to the compound/composition of step a);
c) optionally concentrating the composition of step b) or adding an antisolvent to the composition of step b);
d) crystallizing;
e) optionally evaporating to dryness or equilibrating the obtained suspension of step d); and
f) isolating the obtained precipitate.

In the meaning of the present invention, an antisolvent is a solvent that causes precipitation when added to a solution in another solvent.

The multi-component crystals of the present invention are generally obtained as a fine powder with typical particle size distributions with the median size between 0.1 and 100 µm, preferably between 1 and 50 µm, preferably between 1 to 10 µm. This particle size range ensures a fast dissolution profile, while retaining the favorable handling properties in the formulation process.

The multi-component crystals of the present invention may be used in pharmaceutical com-positions in the same way as other forms of Vismodegib previously known. Additionally, the present multi-component crystals may be employed as intermediates or starting materials to produce the pure active ingredient.

A further aspect of the present invention is a pharmaceutical composition comprising, as active ingredient, multi-component crystals according to the present invention, preferably multi-component crystals as described herein above as being preferred, and preferably further comprising one, two, three, or more pharmaceutically acceptable carriers, and/or diluents, and/or further ingredients, in particular one, two, three, or more pharmaceutical excipients.

The amount of the multi-component crystals in the composition depends on the type of formulation and the desired dosage regimen during administration time periods. The Vismodegib amount in the multi-component crystals in each oral formulation may be from 0.1 to 500 mg, preferably from 20 to 250 mg, in particular from 50 to 200 mg.

Oral formulations (as preferred pharmaceutical compositions according to the present invention) may be solid formulations such as capsules, tablets, pills and troches, or a liquid suspension formulation.

The multi-component crystals according to the invention may be used directly in the form of powders, granules, suspensions, or they may be combined together with other pharmaceutically acceptable ingredients in admixing the components and optionally finely divide them, and then filling capsules, composed for example from hard or soft gelatin, compressing tablets, pills or troches, or suspend in suspensions. Coatings may be applied after compression to form pills.

Pharmaceutically acceptable ingredients are well known for the various types of formulation and may be for example binders such as natural or synthetic polymers, excipients, disintegrants, lubricants, surfactants, sweetening and other flavouring agents, coating materials, preservatives, dyes, thickeners, adjuvants, antimicrobial agents and carriers for the various formulation types.

Examples for binders are gum tragacanth, acacia, starch, gelatin, and biological degradable polymers such as homo- or co-polyesters of dicarboxylic acids, alkylene glycols, polyalkylene glycols and/or aliphatic hydroxyl carboxylic acids; homo- or copolyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers may be linear, branched or crosslinked. Specific examples are poly-glycolic acid, polylactic acid, and poly-d,l-lactide/glycolide. Other examples for polymers are water-soluble polymers such as polyoxaalkylenes (polyoxaethylene, polyoxapropylene and mixed polymers thereof, poly-acrylamides and hydroxylalkylated polyacrylamides, poly-maleic acid and esters or -amides thereof, poly-acrylic acid and esters or -amides thereof, poly-vinylalcohol and esters or -ethers thereof, polyvinylimidazole poly-vinylpyrrolidon, and natural polymers like chitosan, carragenan or hyaluronic acid.

Examples for excipients are phosphates such as dicalcium phosphate.

Examples for disintegrants are croscarmellose sodium, crospovidone, low-substituted hydroxypropyl cellulose, sodium starch glycolate or alginic acid.

Surfactants may be anionic, cationic, amphoteric or neutral. Examples for surfactants are lecithin, phospholipids, octyl sulfate, decyl sulfate, dodecyl sulfate, tetradecyl sulfate, hexadecyl sulfate and octadecyl sulfate, Na oleate or Na caprate, 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or -distearate, glycerol mono- or -dioleate and glycerol mono- or -dipalmitate, and polyoxyethylene stearate.

Examples for sweetening agents are sucrose, fructose, lactose or aspartame.

Examples for flavouring agents are peppermint, oil of wintergreen or fruit flavours like cherry or orange flavour.

Examples for coating materials are gelatin, wax, shellac, sugar or biological degradable polymers.

Examples for preservatives are methyl or propylparabens, sorbic acid, chlorobutanol, phenol and thimerosal.

Examples for adjuvants are fragrances.

Examples for thickeners are synthetic polymers, fatty acids and fatty acid salts and esters and fatty alcohols.

Examples for solid carriers are talc, clay, microcrystalline cellulose, lactose monohydrate, silica, alumina and the like.

The formulation according to the invention may also contain isotonic agents, such as sugars, buffers or sodium chloride.

The multi-component crystals of the present invention may also be formulated as effervescent tablet or powder, which can disintegrate in an aqueous environment to provide a drinking solution.

The most preferred route is oral administration. The dosages may be conveniently presented in a unit dosage form and prepared by any of the methods well-known in the art of pharmacy.

Capsule dosages, of course, will contain the solid composition within a capsule which may be made of gelatin or other conventional encapsulating material. Tablets and powders may be coated. Tablets and powders may be coated with an enteric coating. The enteric coated powder forms may have coatings comprising phthalic acid cellulose acetate, hydroxypropylmethyl-cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

The multi-component crystals of the present invention and its formulations, respectively, can also be administered in combination with other therapeutic agents being effective to treat a given condition and/or to provide a combination therapy.

The multi-component crystals of the present invention and the respective pharmaceutical compositions are useful in the treatment of basal-cell carcinoma (BCC).

The multi-component crystals of the present invention may be used as single component or as mixtures with other solid forms, which may be crystalline or amorphous.

In view of the above, the present invention also relates to multi-component crystals of the present invention and pharmaceutical compositions according to the invention for use as a medicament, preferably for use in the treatment of cancer, in particular for use in the treatment of basal-cell carcinoma (BCC).

In the following, the present invention will be described more closely by way of selected examples illustrating the invention.

Wherever noted, in the following, room temperature depicts a temperature from the range 22-25° C., ambient temperature is defined as 25±10° C. and percentages are given by weight, if not indicated otherwise.
Abbreviations:
DMSO dimethyl sulfoxide
NMR nuclear magnetic resonance (H-NMR denoting to proton NMR)
TG thermogravimetry
r.h. relative humidity (air, if not indicated otherwise)
v/v volume by volume
PXRD powder X-ray diffraction
DSC differential scanning calorimetry
Instrumental:
Powder X-Ray Diffraction:

The measurements were carried out with a Panalytical X'Pert Pro diffractometer (manufacturer: Panalytical) using Cu Kα radiation in the Bragg-Brentano reflection geometry. Generally, the 2θ values are accurate within an error of ±0.1-0.2°. The relative peak intensities can vary considerably for different samples of the same crystalline form because of different preferred orientations of the crystals. The same were prepared without any special treatment other than the application of slight pressure to get a flat surface. Generally, silicon single crystal sample holders of 0.1-1.0 mm depth were used. The tube voltage and current were 45 kV and 40 mA, respectively. Diffraction patterns were recorded in the range from 2θ=3°-35° with increments of 0.0167°. The samples were rotated during the measurement.
Thermogravimetry:

Thermogravimetry is a well known method that allows monitoring the mass loss of a given sample upon heating. Thermogravimetry was performed on a Seico TG/DTA 7200. The measurements were carried out with platinum crucibles under a nitrogen atmosphere and at a heating rate of 10° C./min over the range 30-410° C. or below.
Differential Scanning Calorimetry (DSC):

DSC was performed on a Mettler Toledo DSC 823e module. The sample was placed in crimped but vented aluminium pans. The heating rate was 10° C. per minute and the samples were exposed to a nitrogen stream of 150 mL/min.
$^1$H-NMR:

The $^1$H-NMR spectra were recorded on a Bruker DRX 500 spectrometer using deuterated solvents.
Solvents:

For all experiments, standard grade solvents are used.

EXAMPLES

Vismodegib Maleic Acid Co-Crystal 1:2

The Vismodegib maleic acid co-crystal 1:2 is prepared from Vismodegib and maleic acid. The PXRD pattern is displayed in FIG. 1. Characteristic PXRD peaks (expressed in °2θ±0.2 °2θ; Cu Kα radiation) are observed at 6.7, 13.1, 15.8, 19.5, 27.0, especially at 6.7, 10.7, 13.1, 15.8, 18.0, 19.5, 20.1, 20.4, 21.8, 22.3, 25.4, 26.1, 27.0, 27.4, 27.9, 28.3, 29.0, 29.3. The PXRD pattern complies with the result of the single crystal structure (Table 1). The co-crystal crystallizes in the monoclinic space group P2$_1$. The stoichiometry of the co-crystal can be proven by the crystal structure. The crystal structure also shows that no protonation/deprotonation is present. Unit cell dimensions are shown in Table 1.

TABLE 1

Crystallographic data for Vismodegib maleic acid co-crystal 1:2.

| | |
|---|---|
| crystal system | monoclinic |
| space group | P2$_1$ |
| a (Å) | 5.05640 (10) |
| b (Å) | 26.1914 (6) |
| c (Å) | 10.7941 (3) |
| α (°) | 90.00 |
| β (°) | 102.1710 (10) |
| γ (°) | 90.00 |
| V (Å$^3$) | 1397.38 (6) |
| Z | 2 |
| T (K) | 100 (2) |
| ρ$_{calc}$ (g/cm$^3$) | 1.553 |
| μ (mm$^{-1}$) | 3.375 |
| λ (Å) | 1.54178 |
| reflections collected | 9031 |
| θ range (°) | 3.37-58.97 |
| unique reflns | 3384 |
| largest diff peak and hole (eÅ$^{-3}$) | 0.364/−0.255 |

Example 1

314 mg Vismodegib and 86 mg maleic acid are suspended in toluene saturated with maleic acid for 2 d, filtered and dried.

TG data shows a mass loss of about 2.3 wt % between 100 and 118° C. which is attributed to rest solvent. DSC data shows a single endothermal peak with an onset of about 115° C. (99 J/g).

H-NMR spectroscopy indicates a molar ratio of Vismodegib to maleic acid of about 1:1.3. However single crystal X-ray data confirms a ratio of 1:2 (Table 1).

Example 2

200 mg Vismodegib and 110 mg maleic acid are suspended in 3 mL ethyl acetate, stirred, heated to 75° C. and kept at this temperature for 1 h. The temperature is decreased by about 10° C./min. The solid is filtered and dried.

Yield: about 170 mg (about 55%).

TG data shows no mass loss up to 120° C. where decomposition starts.

Example 3

500 mg Vismodegib and 275 mg maleic acid are suspended in 3 mL ethyl acetate, stirred, heated to 75° C. and kept at this temperature for 1 h. The temperature is decreased by about 10° C./min. The solid is filtered and dried.

Yield: about 552 mg (about 55%).

H-NMR spectroscopy indicates a molar ratio of Vismodegib to maleic acid of about 1:2. TG data shows no mass loss up to 120° C. where decomposition starts. DSC data shows a first endothermal peak with an onset of about 126° C. (138 J/g).

Vismodegib N-Cyclohexyl-Sulfamic Acid Co-Crystals

Two forms of Vismodegib N-cyclohexyl-sulfamic acid co-crystals can be prepared.

a) Vismodegib N-Cyclohexyl-Sulfamic Acid Co-Crystal Form A

The Vismodegib N-cyclohexyl-sulfamic acid co-crystal form A, ratio 1:1 is prepared from Vismodegib and N-cyclohexyl-sulfamic acid.

Figure 2:
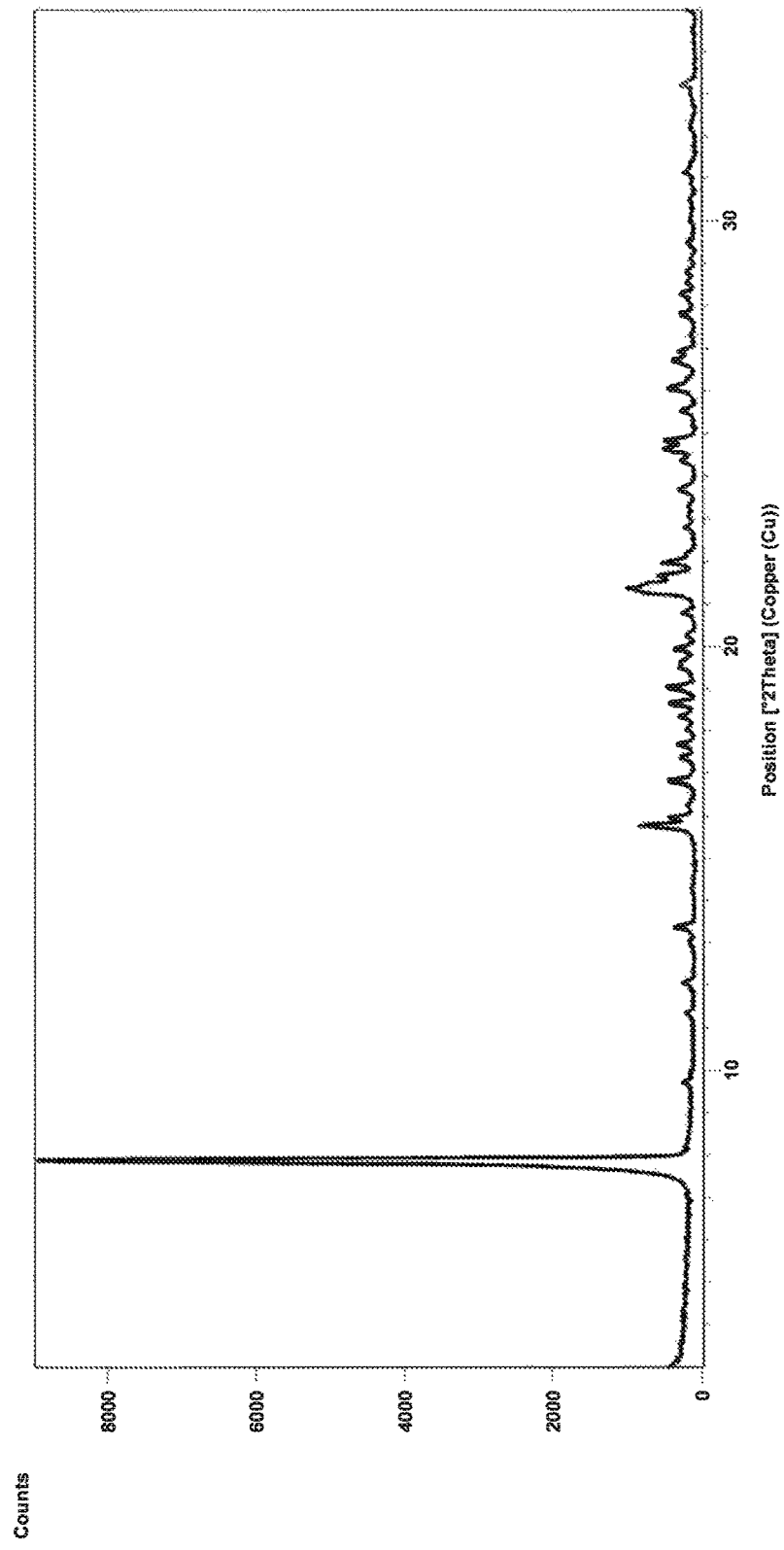
FIG. 2: PXRD pattern of Vismodegib N-cyclohexyl-sulfamic acid co-crystal form A; Cu Kα radiation.

The PXRD pattern is displayed in FIG. 2. Characteristic PXRD peaks (expressed in °2θ±0.2 °2θ; Cu Kα radiation) are observed at 13.4, 16.8, 22.0, 24.8, 26.1 especially at 7.9, 11.3, 12.1, 13.4, 15.8, 16.0, 16.8, 17.6, 18.6, 19.0, 19.9, 21.3, 21.7, 22.0, 24.6, 24.8, 26.1, 26.7.

Single crystals of Vismodegib N-cyclohexyl-sulfamic acid co-crystal form A are obtained. The stoichiometry of the co-crystal can be proven by the crystal structure.

Example 4

281 mg VIS and 219 mg N-cyclohexyl-sulfamic acid are suspended in saturated N-cyclohexyl-sulfamic acid solution in toluene for 2 d, filtered and dried.

H-NMR spectroscopy indicates a molar ratio of Vismodegib to N-cyclohexyl-sulfamic acid of about 1:1.

TG data shows a mass loss of about 3.3 wt % between room temperature and 130° C. DSC data shows a first endothermal event with an onset of about 123° C. (95 J/g).

b) Vismodegib N-Cyclohexyl-Sulfamic Acid Co-Crystal Form B

The Vismodegib N-cyclohexyl-sulfamic acid co-crystal form B is prepared from Vismodegib and N-cyclohexyl-sulfamic acid.

Figure 3:
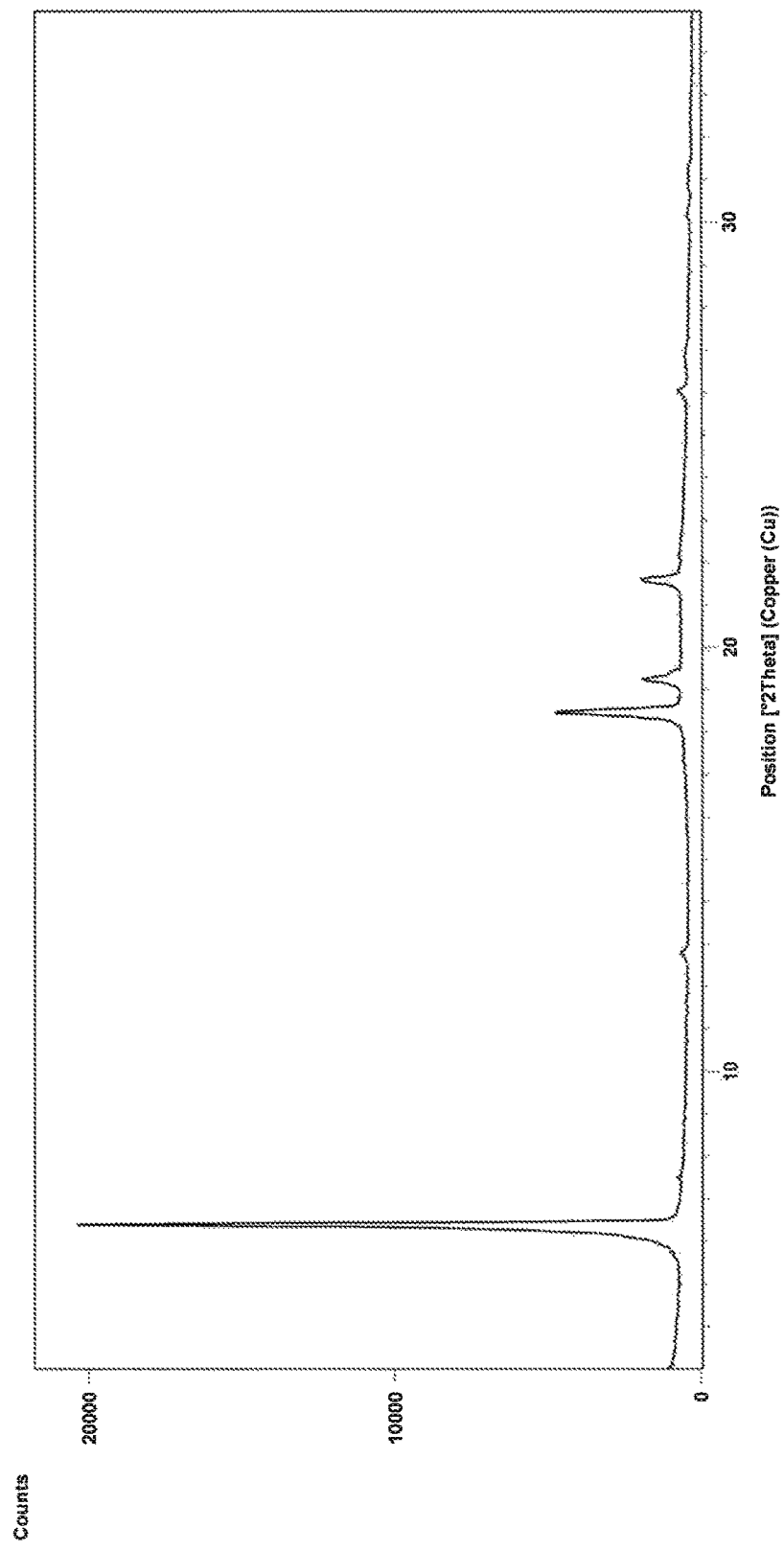
FIG. 3: PXRD pattern of Vismodegib N-cyclohexyl-sulfamic acid co-crystal form B; Cu Kα radiation.

The PXRD pattern is displayed in FIG. 3. Characteristic PXRD peaks (expressed in °2θ±0.2 °2θ; Cu Kα radiation) are observed at 6.4, 12.8, 18.5, 19.2, 21.6, 26.0. Single crystals of Vismodegib N-cyclohexyl-sulfamic acid co-crystal form B are obtained. The stoichiometry of the co-crystal can be proven by the crystal structure.

Example 5

200 mg Vismodegib and 170 mg N-cyclohexyl-sulfamic acid are suspended in 3 mL ethyl acetate and stirred at 75° C. for 24 h. The temperature is decreased by about 10° C./min. The solid is filtered and dried.

Yield: about 212 mg

Vismodegib Sorbitol Co-Crystal 1:1

Figure 4:
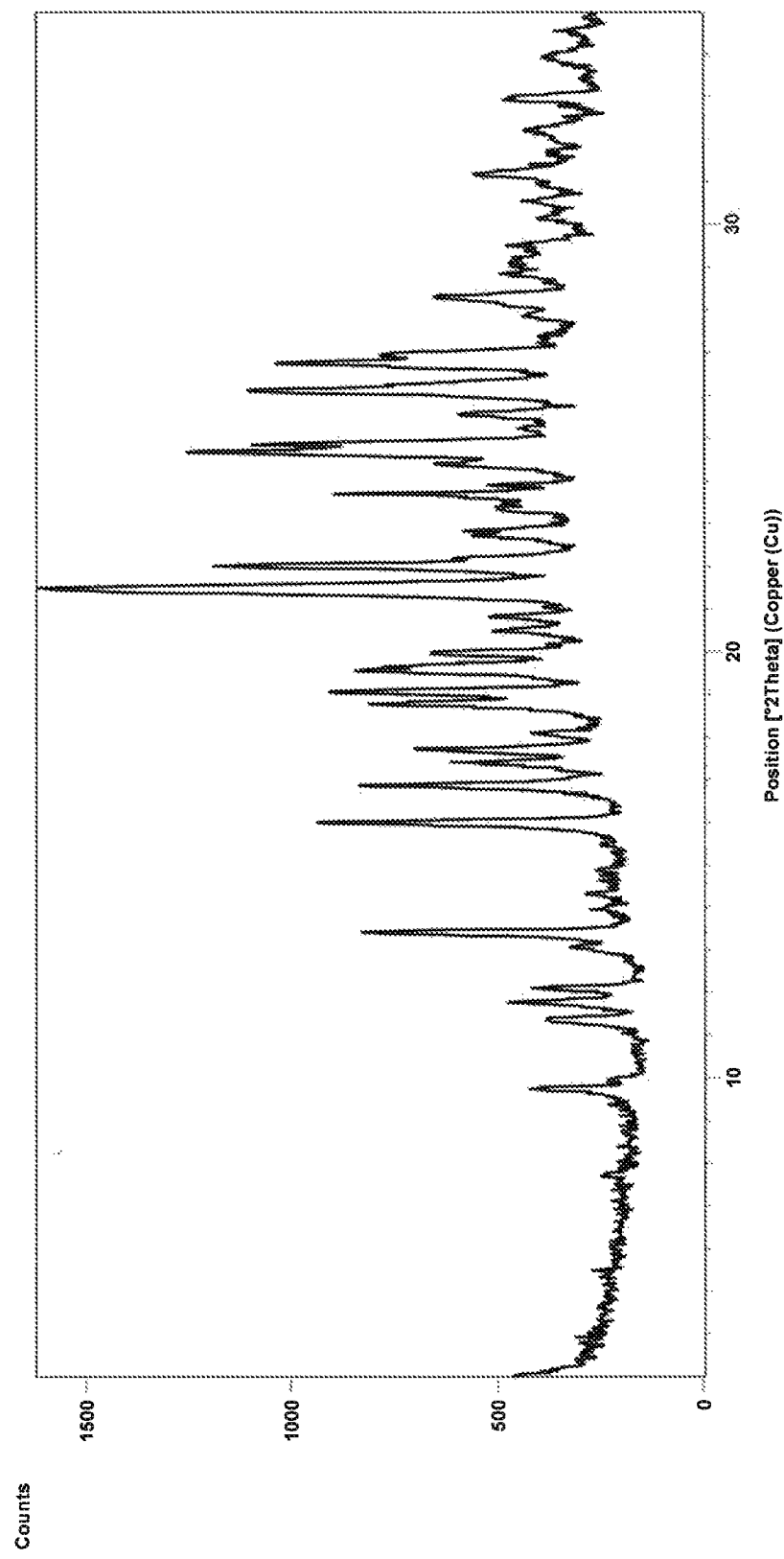
FIG. 4: PXRD pattern of Vismodegib sorbitol co-crystal 1:1; Cu Kα radiation.

The Vismodegib sorbitol co-crystal 1:1 is prepared from Vismodegib and sorbitol. The PXRD pattern is displayed in FIG. 4. Characteristic PXRD peaks (expressed in °2θ±0.2 °2θ; Cu Kα radiation) are observed at 13.4, 16.0, 16.9, 21.5, 22.0, especially at 9.8, 11.4, 12.1, 13.4, 16.0, 16.9, 17.4, 17.7, 18.1, 19.1, 19.5, 20.0, 21.5, 22.0, 24.7, 24.9, 26.1, 26.7.

Single crystals of Vismodegib sorbitol co-crystal 1:1 are obtained. The stoichiometry of the co-crystal can be proven by the crystal structure.

Example 6

280 mg VIS and 120 mg sorbitol are suspended in toluene for 2 d, filtered and dried. H-NMR spectroscopy indicates a molar ratio of Vismodegib to sorbitol of about 1:1. TG data shows a mass loss of about 7 wt % (0.5 mol toluene) between 100 and 160° C. DSC data shows a first endothermal peak with an onset of about 96° C. (49 J/g) and further endothermal peaks at onset points of 156° C. (35 J/g) and 181° C. (58 J/g).

Vismodegib Xylitol Co-Crystal 1:1

The Visnnodegib xylitol co-crystal 1:1 is prepared from Vismodegib and xylitol.

Figure 5:
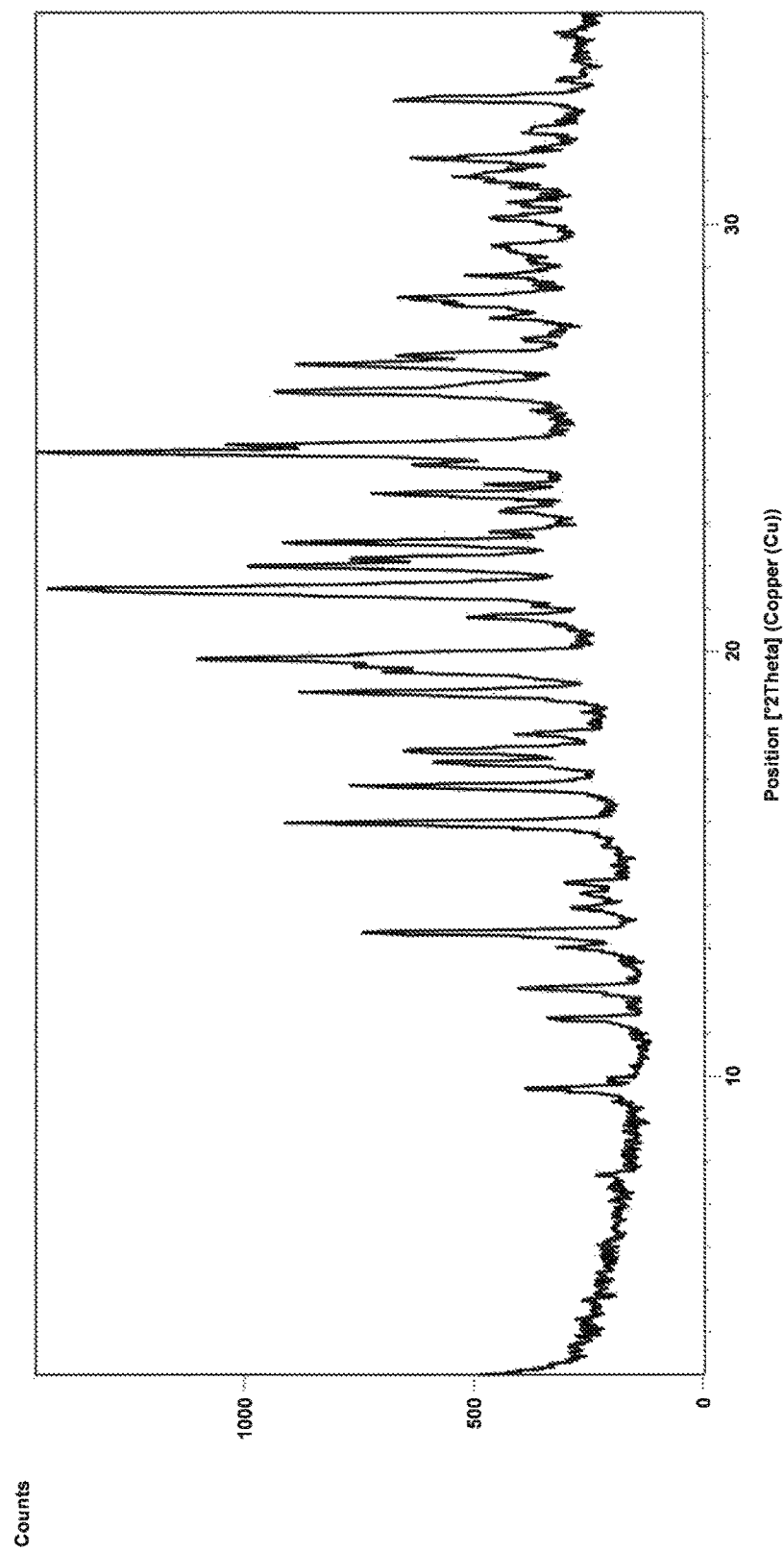
FIG. 5: PXRD pattern of Vismodegib xylitol co-crystal 1:1; Cu Kα radiation.

The PXRD pattern is displayed in FIG. 5. Characteristic PXRD peaks (expressed in °2θ±0.2 °2θ; Cu Kα radiation) are observed at 9.7, 13.4, 16.0, 21.5, 24.6, especially at 9.7, 11.4, 12.1, 13.4, 16.0, 16.8, 17.4, 17.6, 18.0, 19.0, 19.8, 21.5, 22.0, 22.5, 23.7, 24.6, 24.8, 26.1, 26.7, 27.0, 31.5, 32.9.

Single crystals of Vismodegib xylitol co-crystal 1:1 are obtained. The stoichiometry of the co-crystal can be proven by the crystal structure.

Example 7

294 mg VIS and 106 mg xylitol are suspended in toluene for 2 d, filtered and dried. H-NMR spectroscopy indicates a molar ratio of Vismodegib to xylitol of about 1:1. TG data shows a mass loss of about 7 wt % (0.5 mol toluene) between 100 and 150° C. DSC data shows a first endothermal peak with an onset of about 92° C. (52 J/g) and further endothermal peaks at onset points of 155° C. (31 J/g) and 178° C. (55 J/g).

Vismodegib Benzylamine Solvate 2:1

The Vismodegib benzylamine solvate 2:1 is prepared from suspension of Vismodegib in benzylamine.

Figure 6:
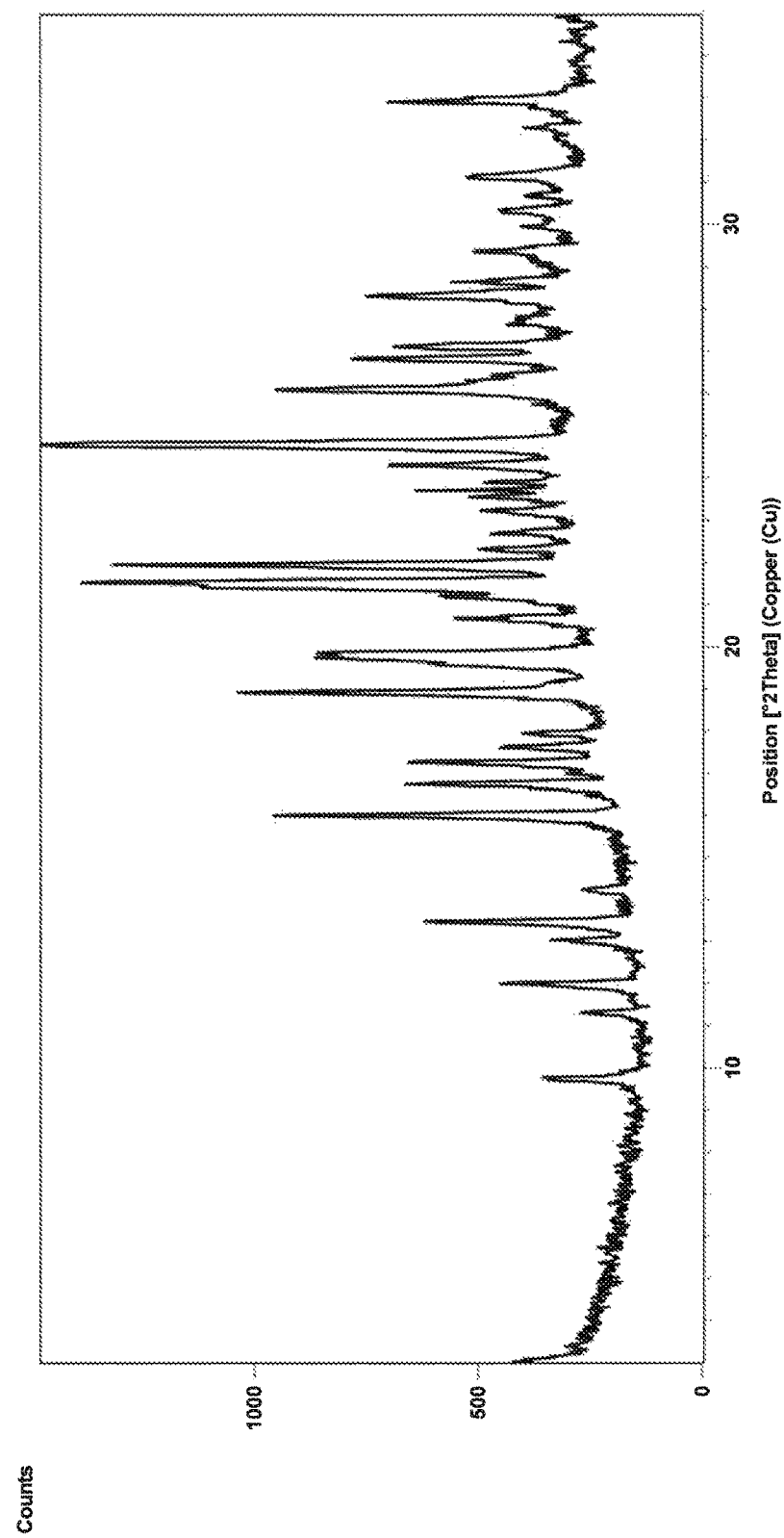
FIG. 6: PXRD pattern of Vismodegib benzylamine co-crystal 2:1; Cu Kα radiation.

The PXRD pattern is displayed in FIG. 6. Characteristic PXRD peaks (expressed in °2θ±0.2 °2θ; Cu Kα radiation) are observed at 9.8, 13.5, 16.0, 18.9, 21.9, 24.7, especially at 9.8, 11.3, 12.0, 13.5, 16.0, 16.7, 17.3, 17.6, 17.9, 18.9, 20.7, 21.5, 21.9, 22.7, 24.3, 24.7, 26.1, 26.8, 27.1, 28.3, 28.6. The PXRD pattern complies with the result of the single crystal structure (Table 2).

Single crystals of Vismodegib benzylamine solvate 2:1 are obtained. The co-crystal crystallizes in the monoclinic space group P21. Unit cell dimensions are shown in Table 2. The stoichiometry of the solvate can be proven by the crystal structure.

TABLE 2

| Crystallographic data for Vismodegib benzylamine solvate 2:1. | |
|---|---|
| crystal system | monoclinic |
| space group | $P2_1$ |
| a (Å) | 11.5307 (14) |
| b (Å) | 10.1979 (13) |
| c (Å) | 18.314 (2) |
| α (°) | 90.00 |
| β (°) | 101.670 (4) |
| γ (°) | 90.00 |
| V (Å$^3$) | 2109.0 (4) |
| Z | 4 |
| T (K) | 100 (2) |
| $\rho_{calc}$ (g/cm$^3$) | 1.554 |
| μ (mm$^{-1}$) | 3.976 |

TABLE 2-continued

Crystallographic data for Vismodegib benzylamine solvate 2:1.

| | |
|---|---|
| λ (Å) | 1.54178 |
| reflns collected | 12354 |
| θ range (°) | 3.91-63.42 |
| unique reflns | 2865 |
| largest diff peak and hole (eÅ$^{-3}$) | -0.672/-0.500 |

Example 8

200 mg Vismodegib are suspended in 0.25 mL benzylamine and stirred for 3 days at room temperature, filtered and dried in vacuum.

H-NMR spectroscopy indicates a molar ratio of Vismodegib to benzylamine of about 2:1.

TG data shows a mass loss of about 11.4% between 100 and 170° C. (theoretical benzylamine content 11.3%). DSC data in a closed sample pan shows a first endothermal peak with an onset of about 151° C. (72 J/g).

Example 9

200 mg Vismodegib are suspended in 255 mg benzylamine and 1 mL heptane and stirred at 50° C. for 28 h. The temperature is decreased by about 10° C./min. The solid is filtered and dried.

TG data shows a mass loss of about 10.8% between 100 and 170° C. (theoretical benzylamine content 11.3%). DSC data in a closed sample pan shows a first endothermal peak with an onset of about 150° C. (96 J/g).

Example 10

260 mg Vismodegib are suspended in 434 mg benzylamine and 2 mL heptane and stirred at 50° C. for 24 h, temperature cycled between 25 and 50° C. for 5 days, filtered and dried in vacuum.

Vismodegib Triethanolamine Solvate

The Vismodegib triethanolamine solvate can be prepared from Vismodegib and triethanolamine.

Figure 7:
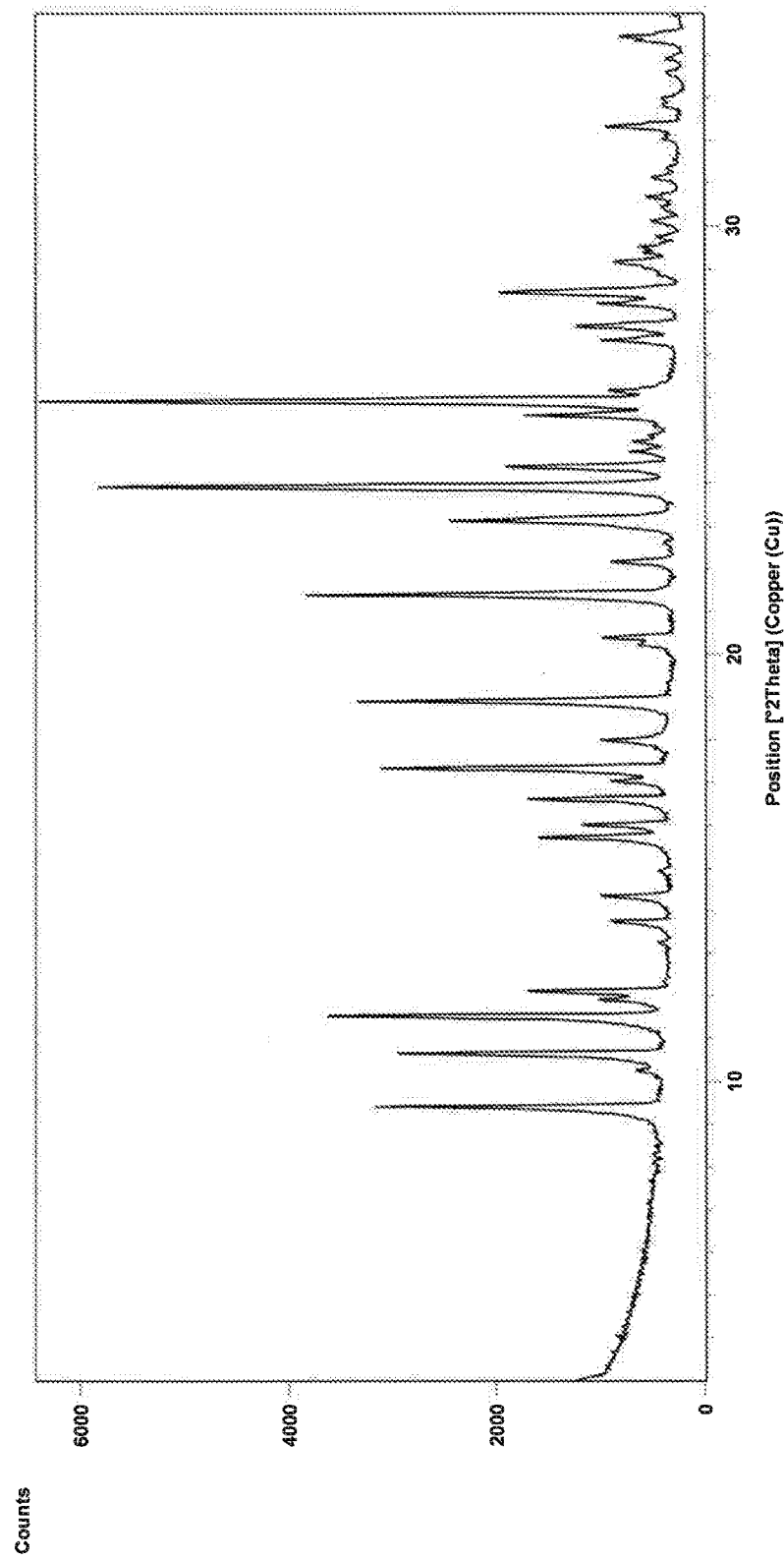
FIG. 7: PXRD pattern of Vismodegib triethanolamine co-crystal; Cu Kα radiation.

The PXRD pattern is displayed in FIG. 7. Characteristic PXRD peaks (expressed in 2θ±0.2°2θ; Cu Kα radiation) are observed at 9.4, 11.5, 21.4, 23.9, 25.9, especially at 9.4, 10.7, 11.5, 12.1, 13.7, 14.3, 15.7, 16.0, 16.6, 17.3, 18.0, 18.9, 21.4, 22.2, 23.1, 23.9, 24.4, 25.6, 25.9, 27.3, 27.7, 28.4.

Single crystals of Vismodegib triethanolamine solvate are obtained. The stoichiometry of the solvate can be proven by the crystal structure.

Example 11

300 mg Vismodegib are suspended in 730 mg triethanolamine and 1 mL acetone and stirred at room temperature for 14 days, filtered and dried.

H-NMR spectroscopy indicates a molar ratio of Vismodegib to triethanolamine of about 1:0.9.

TG data shows a mass loss of about 2.1% between room temperature and 100° C. and no further significant weight loss up to 150° C. DSC data in a closed sample pan shows a first endothermal peak with an onset of about 135° C. (77 J/g).

The invention claimed is:

1. A multi-component crystal comprising Vismodegib, which is a compound of formula 1,

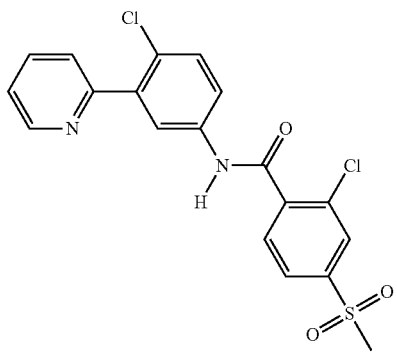

formula 1 and a second compound which is a compound in the solid state and is a co-crystal former selected from the group consisting of maleic acid, N-cyclohexyl-sulfamic acid, sorbitol and xylitol and a solvent which is selected from the group consisting of benzylamine and triethanolamine.

2. The multi-component crystal according to claim 1, wherein the molar ratio of Vismodegib to the second compound is in the range of from 3:1 to 1:3.

3. The multi-component crystal according to claim 1, wherein the second compound is maleic acid and the multi-component crystal has a PXRD pattern with at least one characteristic peak, expressed in °2θ±0.2 °2θ using CuKα radiation, selected from the following peaks located at 6.7, 10.7, 13.1, 15.8, 18.0, 19.5, 20.1, 20.4, 21.8, 22.3, 25.4, 26.1, 27.0, 27.4, 27.9, 28.3, 29.0, 29.3.

4. The multi-component crystal according to claim 1, wherein the second compound is N-cyclohexyl-sulfamic acid and the multi-component crystal has a PXRD pattern with at least one characteristic peak, expressed in °2θ±0.2 °2θ using CuKα radiation, selected from the following peaks located at 7.9, 11.3, 12.1, 13.4, 15.8, 16.0, 16.8, 17.6, 18.6, 19.0, 19.9, 21.3, 21.7, 22.0, 24.6, 24.8, 26.1, 26.7.

5. The multi-component crystal according to claim 1, wherein the second compound is N-cyclohexyl-sulfamic acid and the multi-component crystal has a PXRD pattern with at least one characteristic peak, expressed in °2θ±0.2 °2θ using CuKα radiation, selected from the following peaks located 6.4, 12.8, 18.5, 19.2, 21.6, 26.0.

6. The multi-component crystal according to claim 1, wherein the second compound is sorbitol and the multi-component crystal has a PXRD pattern with at least one characteristic peak, expressed in °2θ±0.2 °2θ using CuKα radiation, selected from the following peaks located at 9.8, 11.4, 12.1, 13.4, 16.0, 16.9, 17.4, 17.7, 18.1, 19.1, 19.5, 20.0, 21.5, 22.0, 24.7, 24.9, 26.1, 26.7.

7. The multi-component crystal according to claim 1, wherein the second compound is xylitol and the multi-component crystal has a PXRD pattern with at least one characteristic peak, expressed in °2θ±0.2 °2θ using CuKα radiation, selected from the following peaks located at 9.7, 11.4, 12.1, 13.4, 16.0, 16.8, 17.4, 17.6, 18.0, 19.0, 19.8, 21.5, 22.0, 22.5, 23.7, 24.6, 24.8, 26.1, 26.7, 27.0, 31.5, 32.9.

8. The multi-component crystal according to claim 1, wherein the second compound is benzylamine and the multi-component crystal has a PXRD pattern with at least one characteristic peak, expressed in °2θ±0.2 °2θ using CuKα radiation, selected from the following peaks located at 9.8, 11.3, 12.0, 13.5, 16.0, 16.7, 17.3, 17.6, 17.9, 18.9, 20.7, 21.5, 21.9, 22.7, 24.3, 24.7, 26.1, 26.8, 27.1, 28.3, 28.6.

9. The multi-component crystal according to claim 1, wherein the second compound is triethanolamine and the multi-component crystal has a PXRD pattern with at least one characteristic peak, expressed in °2θ±0.2 °2θ using CuKα radiation, selected from the following peaks located at 9.4, 10.7, 11.5, 12.1, 13.7, 14.3, 15.7, 16.0, 16.6, 17.3, 18.0, 18.9, 21.4, 22.2, 23.1, 23.9, 24.4, 25.6, 25.9, 27.3, 27.7, 28.4.

10. A pharmaceutical composition comprising, as active ingredient, the multi-component crystal according to claim 1, and further comprising one, two, three, or more pharmaceutically acceptable carriers, and/or diluents, and/or further ingredients.

11. A pharmaceutical composition comprising, as active ingredient, the multi-component crystal according to claim 1, and further comprising one, two, three, or more pharmaceutically acceptable carriers, and/or diluents, and/or one, two, three, or more pharmaceutical excipients.

12. The pharmaceutical composition according to claim 10, wherein the total amount of Vismodegib in the multi-component crystal in the composition is in the range from 0.1 to 500 mg.

13. The pharmaceutical composition according to claim 10, wherein the total amount of Vismodegib in the multi-component crystal in the composition is in the range from 20 to 250 mg.

14. The pharmaceutical composition according to claim 10, wherein the total amount of Vismodegib in the multi-component crystal in the composition is in the range from 50 to 200 mg.

15. A medicament comprising the multi-component crystal according to claim 1.

16. A process for obtaining the multi-component crystal according to claim 1 comprising the steps of:
a) providing Vismodegib which is a compound of formula 1,

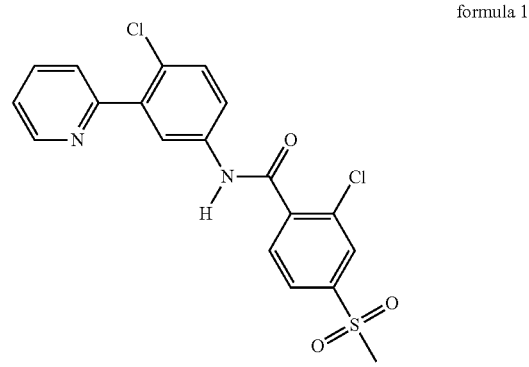 [SMILES: CS(=O)(=O)c1ccc(C(=O)Nc2ccc(Cl)c(-c3ccccn3)c2)c(Cl)c1]

formula 1 as a solid or in solution;
b) adding maleic acid, N-cyclohexyl-sulfamic acid, sorbitol, xylitol, benzylamine or triethanolamine to the compound/composition of step a);
c) optionally concentrating the composition of step b) or adding an antisolvent to the composition of step b);
d) crystallizing;
e) optionally evaporating to dryness or equilibrating the obtained suspension of step d); and
f) isolating the obtained precipitate.

* * * * *